United States Patent
Furnish et al.

(10) Patent No.: US 9,839,769 B2
(45) Date of Patent: Dec. 12, 2017

(54) EXPANDABLE SHEATH ASSEMBLY AND METHOD OF USING SAME

(71) Applicant: Freudenberg Medical, LLC, Carpinteria, CA (US)

(72) Inventors: Greg Furnish, Louisville, KY (US); Anthony Appling, Crestwood, KY (US); Simon Furnish, Louisville, KY (US); Asela Indaka Gunasekara, Louisville, KY (US); Ben Morris, Jeffersonville, IN (US)

(73) Assignee: FREUDENBERG MEDICAL, LLC, Carpinteria, CA (US)

( * ) Notice: Subject to any disclaimer, the term of this patent is extended or adjusted under 35 U.S.C. 154(b) by 390 days.

(21) Appl. No.: 14/477,485

(22) Filed: Sep. 4, 2014

(65) Prior Publication Data

US 2016/0067454 A1   Mar. 10, 2016

(51) Int. Cl.
*A61M 25/06* (2006.01)
*A61M 39/06* (2006.01)
*A61M 29/00* (2006.01)
*A61M 25/00* (2006.01)

(52) U.S. Cl.
CPC ........ *A61M 25/0662* (2013.01); *A61M 39/06* (2013.01); *A61M 29/00* (2013.01); *A61M 2025/0004* (2013.01); *A61M 2025/0024* (2013.01); *A61M 2025/0687* (2013.01); *A61M 2039/062* (2013.01); *A61M 2039/0673* (2013.01)

(58) Field of Classification Search
CPC ............ A61M 29/00; A61M 2025/004; A61M 2025/0024; A61M 2025/0687; A61M 2039/0673; A61M 25/0662; A61M 39/06; A61M 2039/062
See application file for complete search history.

(56) References Cited

U.S. PATENT DOCUMENTS

| | | | |
|---|---|---|---|
| 4,921,479 A | 5/1990 | Grayzel | |
| 5,203,780 A * | 4/1993 | Liebler | A61B 18/22 604/265 |
| 5,256,150 A | 10/1993 | Quiachon et al. | |
| 5,447,503 A * | 9/1995 | Miller | A61M 25/0068 604/528 |
| 5,935,122 A | 8/1999 | Fourkas et al. | |
| 5,997,508 A | 12/1999 | Lunn et al. | |
| 6,183,443 B1 | 2/2001 | Kratoska et al. | |

(Continued)

*Primary Examiner* — Alexander Orkin
(74) *Attorney, Agent, or Firm* — Dickinson Wright PLLC

(57) ABSTRACT

An expandable sheath assembly includes a support body extending from a proximal end to a distal end. A guide rod is interconnected to the support body and extends between the ends along an axis. A dilator extends from the guide rod for insertion into a body vessel, and a hub is releasable connected to the distal end of the support body. A distal sheath overlays the dilator, and a hemostatic valve is slidably disposed along the axis. A proximal sheath extends from the hemostatic valve and is disposed in surrounding and coaxial relationship with the guide rod. The proximal sheath is concurrently slidable with the hemostatic valve along axis to advance the proximal sheath through the hub and interleave the proximal sheath between the dilator and the distal sheath for lifting the distal sheath from the dilator and effectuating an expansion of the body vessel.

19 Claims, 8 Drawing Sheets

(56) References Cited

U.S. PATENT DOCUMENTS

| | | | |
|---|---|---|---|
| 6,443,979 B1 | 9/2002 | Stalker et al. | |
| 2002/0007152 A1* | 1/2002 | Hermann | A61B 17/3462 604/167.04 |
| 2005/0085841 A1 | 4/2005 | Eversull et al. | |
| 2007/0255305 A1* | 11/2007 | McMichael | A61B 17/3421 606/191 |
| 2008/0167606 A1* | 7/2008 | Dann | A61M 25/0119 604/95.04 |
| 2010/0030162 A1* | 2/2010 | Cremascoli | A61M 25/0021 604/246 |
| 2010/0094392 A1 | 4/2010 | Nguyen et al. | |
| 2011/0112567 A1* | 5/2011 | Lenker | A61M 25/0023 606/194 |
| 2014/0025036 A1* | 1/2014 | Bierman | A61M 25/0097 604/506 |

* cited by examiner

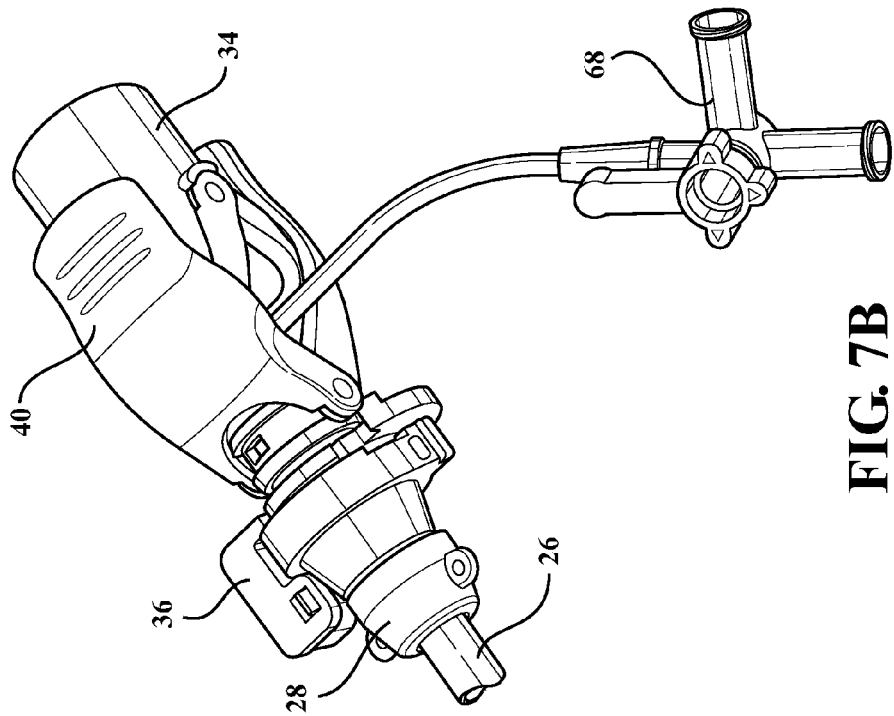
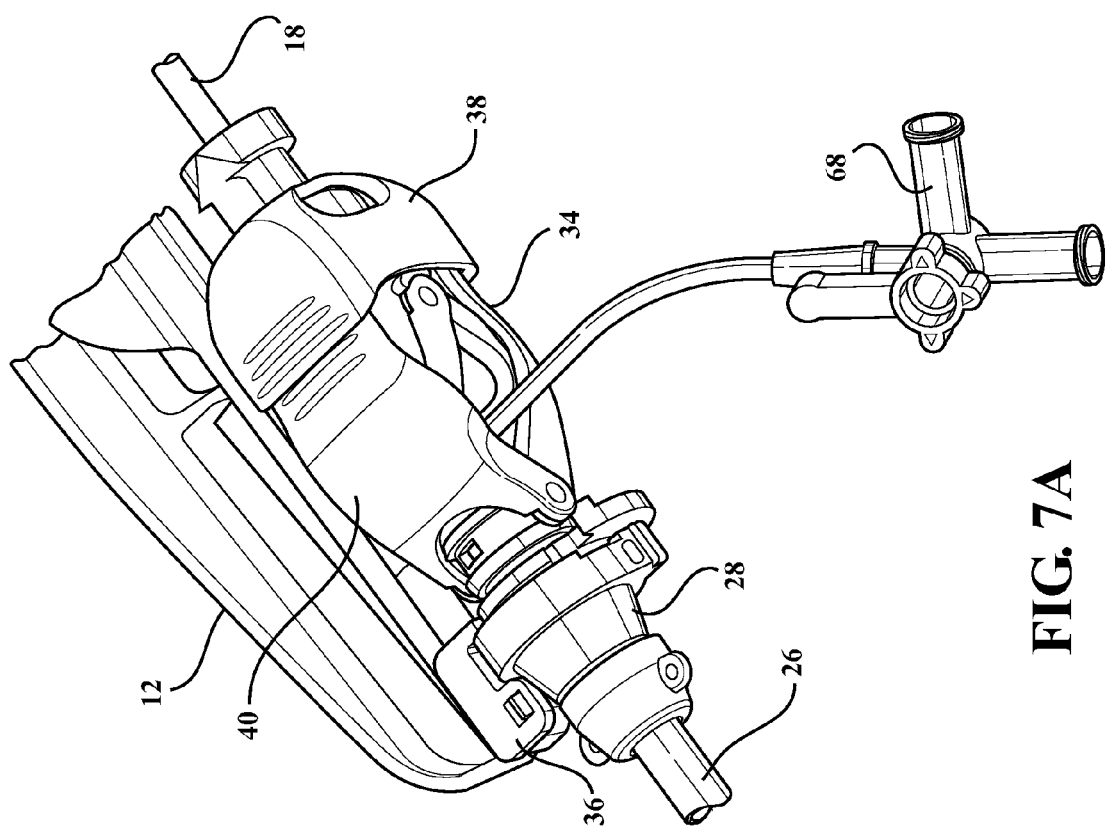

EXPANDABLE SHEATH ASSEMBLY AND METHOD OF USING SAME

BACKGROUND OF THE INVENTION

1. Field of the Invention

The present disclosure relates generally to medical devices and procedures. In particular, the present disclosure relates to expandable sheath assemblies, and methods of using the same.

2. Description of the Prior Art

This section provides background information related to the present disclosure which is not necessarily prior art.

Numerous procedures have been developed that involve the percutaneous insertion of a medical device into the body of a patient, with the medical device being introduced into the body by a variety of known techniques. For example, access to coronary arteries, carotid arteries, the aorta, and peripheral vessels or other tubular members of the body for percutaneous therapeutic, diagnostic, and guide catheters is often made through introducer sheaths which are positioned into body vessels from outside the bodies. Such access sites include, but are not limited to, the common femoral artery/vein and the radial arteries, as well as the ureter, urethra, intestinal track, veins and other tubular tissues. However, the use of introducer sheaths and/or medical devices which are large relative to the body vessels to which they are inserted poses risks and challenges to both the patient and the physician.

For example, relative to femoral sheaths and catheters, larger introducer sheaths create sizeable arteriotomies in the femoral artery which cause more trauma to the patient, such as through artery avulsion, and create more challenges in placement of the sheath with risk of dissection. In addition, the forces required by the physician to insert the larger introducer sheaths and/or medical devices into the body vessel can be higher than desired and create medical issues for the patient if calcification within the body vessel is dislodged during insertion of the introducer sheath and/or medical device.

Methods of accessing a body vessel with a larger introducer sheath and/or medical device can begin by dilating the vessel with a radially expanding intravascular sheath assembly prior to introducing the medical device. However, such radially expanding sheaths have complex mechanisms, such as ratcheting or balloon mechanisms, that expand and maintain the sheath in an expanded configuration while a medical device with a large diameter is introduced. Further, since the mechanisms effectuate the expansion of the body vessel, they do not provide a user with tactile feedback, and can even pose a risk of dissection during the procedure. Accessing the body vessel remains a challenge with existing expandable sheath assemblies due to the relatively large profile of the medical device inserted which causes longitudinal and radial tearing of the vessel during insertion. As mentioned above, these prior art delivery systems can even dislodge calcified plaque within the vessels during insertion, posing an additional risk of clots caused by the dislodged plague.

Accordingly, there remains a need in the art for an improved expandable sheath assembly for use with the percutaneous insertion of a medical device into a body vessel of a patient.

SUMMARY OF THE DISCLOSURE

This section provides a general summary of the disclosure and is not intended to be a comprehensive disclosure of its full scope, aspects, objectives, and/or all of its features.

An expandable sheath assembly for use in inserting a medical device into a body vessel of a patient includes a support body extending from a proximal end to a distal end. A guide rod is interconnected to the support body and extends between the ends along an axis A. The expandable sheath assembly includes a dilator having a low profile diameter which extends from the guide rod to a distal dilator tip for facilitating an initial insertion of the expandable sheath assembly into a body vessel of a patient. A hub is releasable connected to the distal end of the support body and defines a passageway disposed in surrounding and coaxial relationship with the guide rod. A distal sheath comprised of a low friction polymeric material overlays the dilator, and a hemostatic valve is slidably disposed along the axis A. The expandable sheath assembly includes a proximal sheath fixed to the hemostatic valve and which is disposed in surrounding and coaxial relationship with said guide rod. The proximal sheath concurrently slides with the hemostatic valve along the axis A to advance the proximal sheath through the hub and interleave the proximal sheath between the dilator and the distal sheath. As a result, the distal sheath is lifted from the dilator by way of the proximal sheath to effectuate an expansion of the distal sheath within the body vessel.

The subject disclosure also includes a method of inserting an expandable sheath assembly into a body vessel of a patient. The method includes inserting a dilator overlaid with a distal sheath comprised of a low friction polymeric material into a body vessel of a patient. The method proceeds by releasing a hemostatic valve from a proximal end of a support body, with the hemostatic valve including a proximal sheath extending therefrom and disposed in surrounding and coaxial relationship with a guide rod along an axis A. The hemostatic valve is slid along the guide rod to advance the proximal sheath through a hub attached to a distal end of the support body and interleave the proximal sheath between the dilator and the distal sheath.

The subject expandable sheath assembly and method of using same advantageously allows the proximal sheath, which has a larger diameter than a lower profile diameter of the dilator, to be slidably advanced into the body vessel. The lifting of the distal sheath to expand the sheath assembly, and thus the body vessel, also avoids the need to push the proximal sheath past any calcification that is present within the body vessel, and further provides tactile feedback to a user while inserting the proximal sheath into the body vessel. The subject expandable sheath assembly and method also provides for a smaller profile upon initial insertion of the expandable catheter assembly into a body vessel, followed by a method of expansion that reduces trauma on the patient, including a reduction in the shear, hoop stress/dilation, and axial stress on the body vessel. As a result, the subject expandable sheath assembly and method can even reduce the risk of re-access complications in subsequent treatments.

Further areas of applicability will become apparent from the description provided herein. The description and specific examples in this summary are intended for purposes of illustration only and are not intended to limit the scope of the present disclosure.

BRIEF DESCRIPTION OF THE DRAWINGS

The drawings described herein are for illustrative purposes only of selected embodiments, and are not all possible implementations and thus are not intended to limit the scope of the present disclosure.

FIG. 7A illustrates a perspective view of the expandable sheath assembly illustrating the detachable cap disposed over the hemostatic valve to hold a pair of lever arms in a radially compressed position; and FIG. 7B illustrates a perspective view of the expandable sheath assembly illustrating the detachable cap removed from the hemostatic valve to release the pair of lever arms from the radially compressed position.

DESCRIPTION OF THE ENABLING EMBODIMENTS

Example embodiments will now be described more fully with reference to the accompanying drawings. The example embodiments are provided so that this disclosure will be thorough and fully convey the scope to those skilled in the art. Numerous specific details are set forth such as examples of specific components, devices, mechanisms, assemblies, and methods to provide a thorough understanding of various embodiments of the present disclosure. It will be apparent to those skilled in the art that specific details need not be employed, that example embodiments may be embodied in many different forms, and that neither should be construed to limit the scope of the disclosure. With this in mind, the present disclosure is generally directed to expandable sheath assemblies of the type used to introduce and withdrawal a medical device (i.e., catheter systems, implants, etc.) into a body vessel of a patient.

Figure 6:
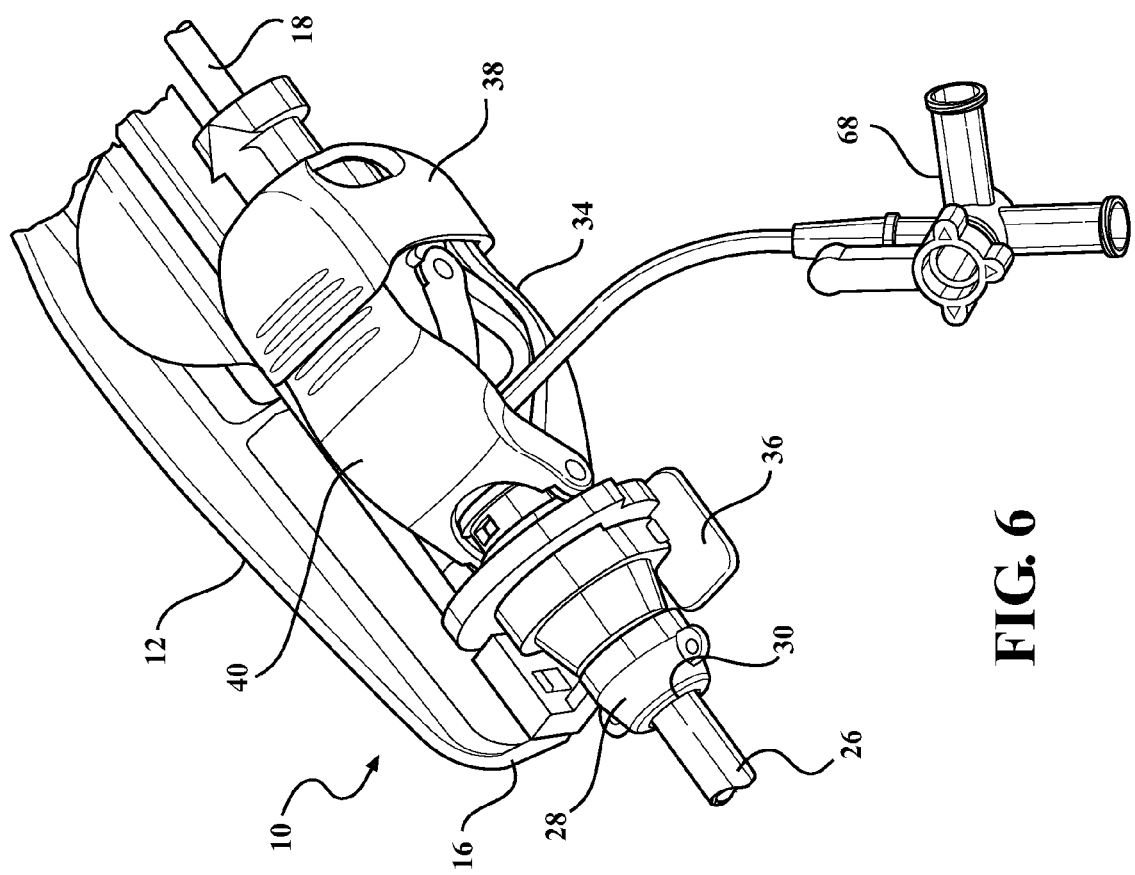
FIG. 6 is a perspective view of the hemostatic valve disposed in abutting relationship with a hub.
Figure 7:
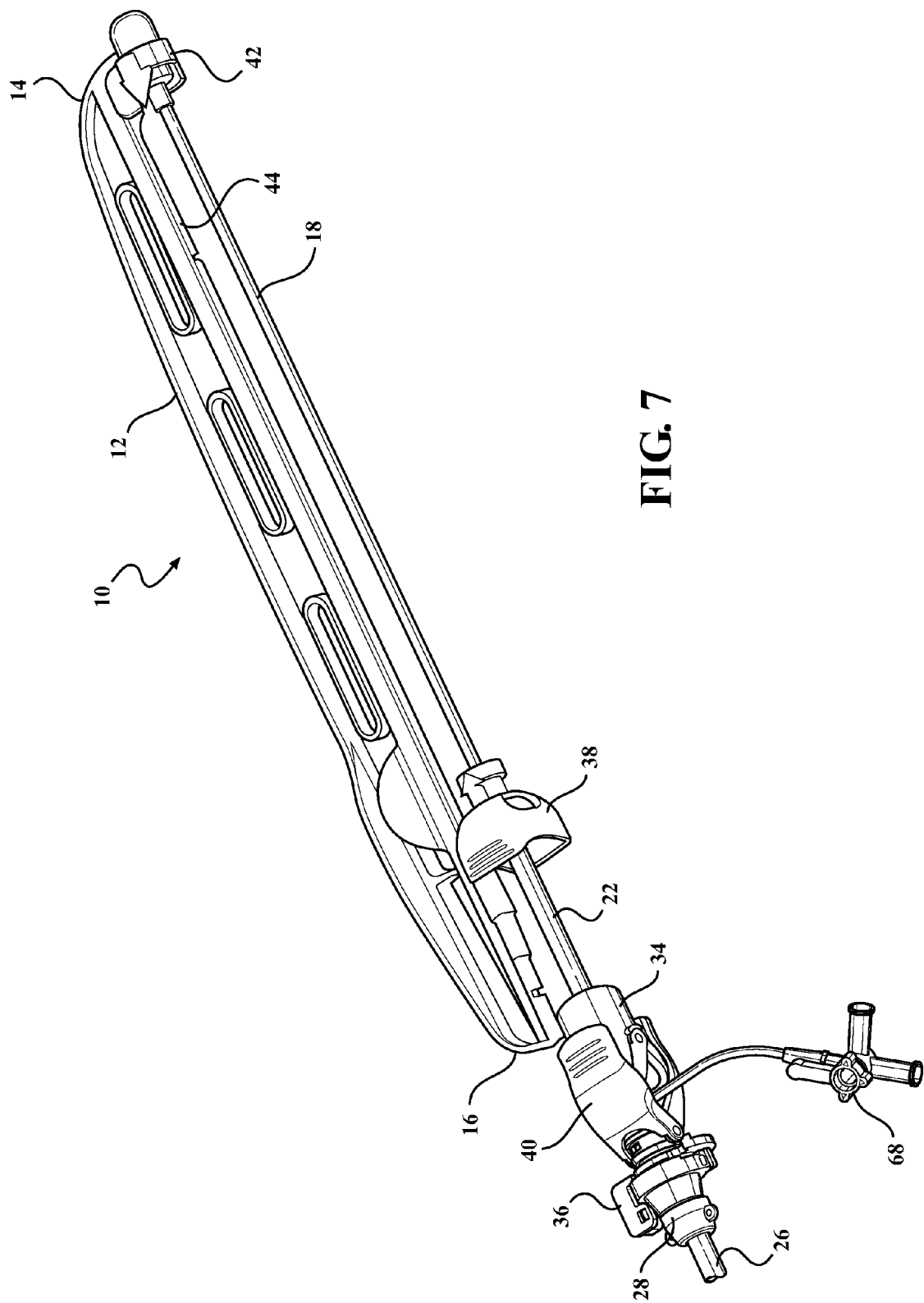
FIG. 7 is a perspective view of the expandable sheath assembly illustrating a detachable cap removed from the hemostatic valve.

Referring to the Figures, wherein like numerals indicate corresponding parts throughout the several views, an expandable sheath assembly 10 for use in inserting a medical device into a body vessel of a patient includes a support body 12 extending from a proximal end 14 to a distal end 16. As best shown in FIGS. 6 and 7, a guide rod 18 is interconnected to the support body 12 and extends between the distal and proximal ends 16, 18 along an axis A. As will be explained in more detail below, the guide rod 18 assists a user with introducing a proximal or introducer sheath 20 into the body vessel of the patient.

Figure 1:
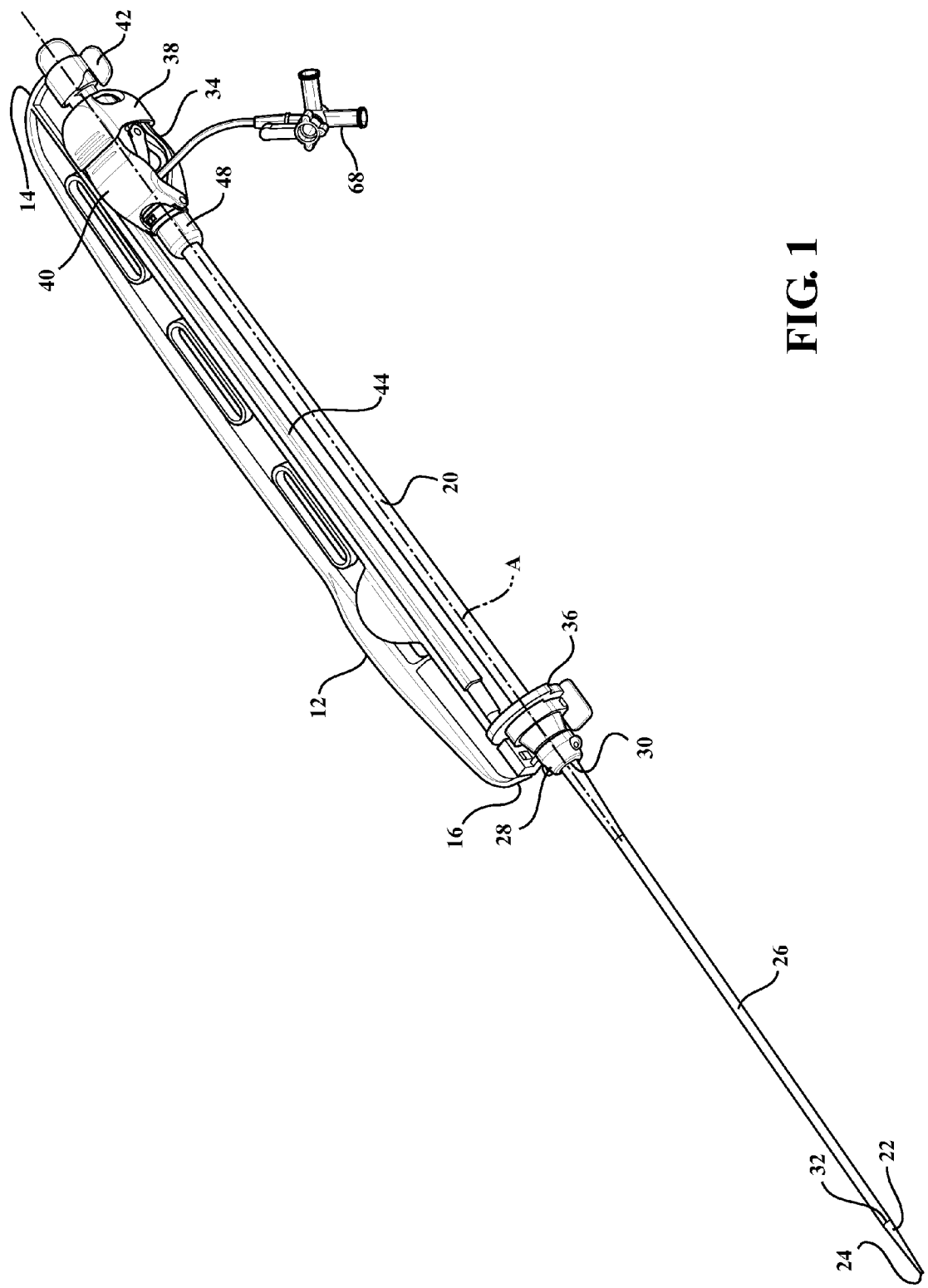
FIG. 1 is a perspective view of an expandable sheath assembly constructed in accordance with the principles of the present disclosure.
Figure 2:
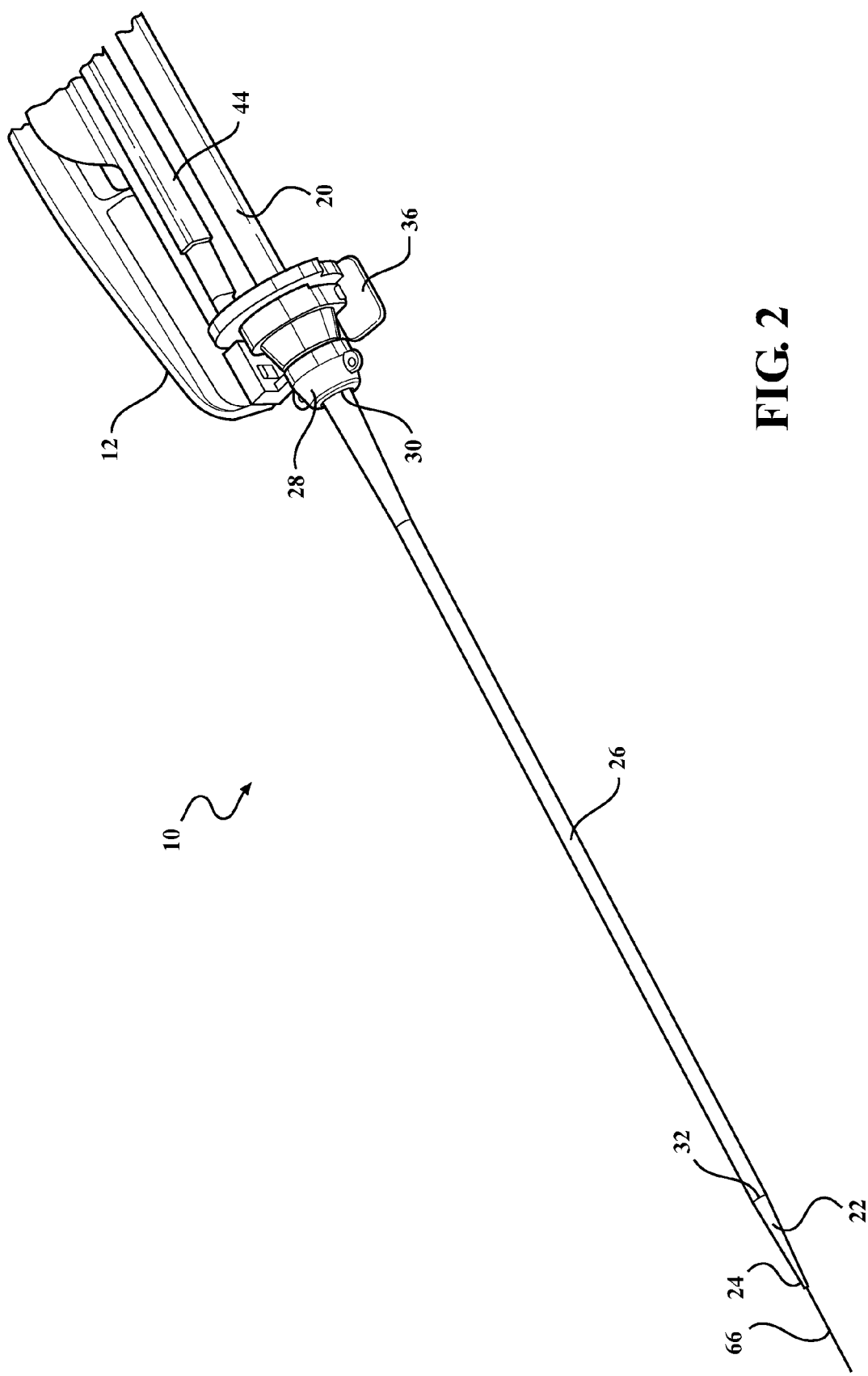
FIG. 2 is an enlarged perspective view of a portion of FIG. 1.
Figure 3:
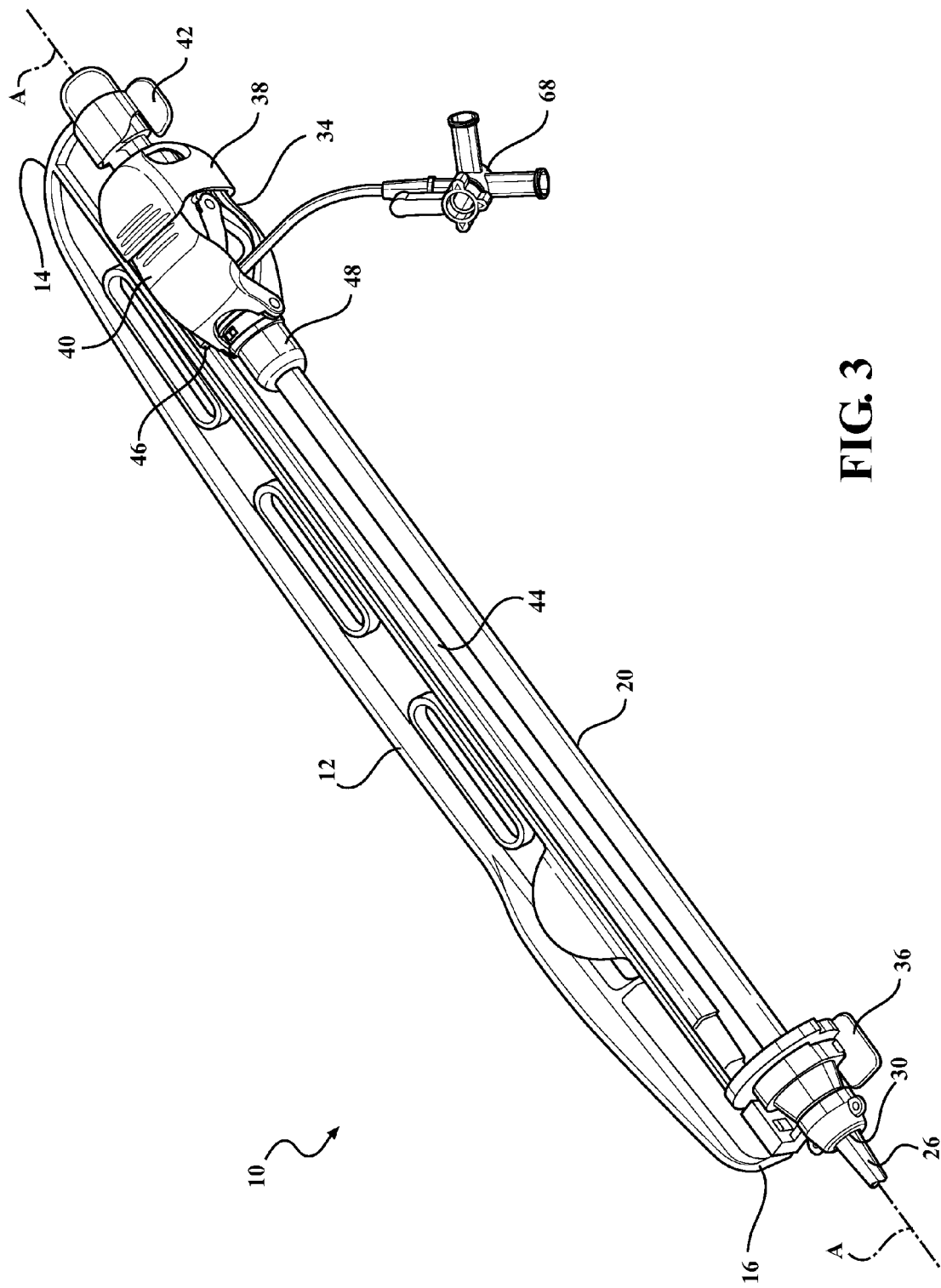
FIG. 3 is a perspective view of the expandable sheath assembly illustrating a dilator and distal sheath initially disposed in a body vessel and a proximal sheath extending along an axis A between a hemostatic valve and a hub.

As best shown in FIGS. 1 and 2, the expandable sheath assembly 10 includes a dilator 22 which extends from the guide rod 18 to a distal dilator tip 24. The dilator 22 has a low profile diameter and is comprised of a flexible polymeric material so that, as shown in FIG. 3, an initial insertion of the expandable sheath assembly 10 into the body vessel of the patient can easily be achieved. A distal sheath 26 overlays the dilator 22 and is comprised of low friction polymeric material for creating a low friction surface of the dilator 22 to ease an insertion of the dilator 22 into the body vessel of the patient. In a preferred embodiment, the low friction polymeric material is expanded polytetrafluoroethylene (ePTFE), however, other suitable low friction polymeric materials could also be used without departing from the scope of the subject disclosure.

As best shown in FIG. 1, the expandable sheath assembly 10 includes a hub 28 interconnected to the distal end 16 of the support body 12, the hub 28 defining a passageway (not expressly shown) disposed in surrounding and coaxial relationship with the guide rod 18. The distal sheath 26 overlays the dilator 22 between a first distal sheath end 30 and a second distal sheath end 32, and in a preferred embodiment is threadingly attached to the hub 28 at the first distal sheath end 30 to dispose the distal sheath 26 in surrounding relationship with the passageway of the hub 28. As further shown in FIG. 1, in a preferred embodiment, the second distal sheath end 32 is releasably attached to the dilator 22 and disposed in spaced relationship with the distal dilator tip 24.

The expandable sheath assembly 10 includes a hemostatic valve 34 slidably disposed about the guide rod 18 for establishing a sliding axial movement along the axis A between the proximal end 14 of the support body 12 and the hub 28. In a preferred embodiment, the hemostatic valve 34 can be a variable diameter seal hemostatic valve as described in co-owned U.S. patent application Ser. No. 14/326,593 entitled "A Medical Valve with a Variable Diameter Seal", the entire disclosure of which is incorporated by reference. However, other valves, such as iris valves, laproscopic ports, slit valves, or the like, can also be utilized without departing from the scope of the subject disclosure.

A proximal introducer sheath 20 is fixed to the hemostatic valve 34 and is disposed in surrounding and coaxial relationship with the guide rod 18 for concurrent sliding movement with the hemostatic valve 34 along the axis A. The proximal sheath 20 has a proximal sheath diameter which is greater than the low profile diameter of the dilator 22 but less than a diameter of the passageway of the hub 28. This allows the proximal sheath 20 to pass through the hub 28 and be concentrically advanced in interleaving relationship between the dilator 22 and the distal sheath 26 during sliding movement of the hemostatic valve 34 along the axis A. The sliding advancement of the proximal sheath 20 through the hub 28 lifts the distal sheath 26 from the dilator 22 to expand the lower profile diameter of the dilator 22 within the body vessel. Put another way, the distal sheath 26 is expanded after it is placed within the body vessel by way of the sliding introduction of the proximal sheath 20 between the dilator 22 and the distal sheath 26. This insertion process is advantageous because it reduces trauma to the body vessel and does not require a pushing of the proximal sheath 20 past any calcification that is present. In addition, the sliding advancement of the proximal sheath 20 through the hub 28 disposes the distal sheath 26 in overlaying relationship with the proximal sheath 20, and thus provides a protective layer for the proximal sheath 20 when disposed within the body vessel. This distal sheath 26 also provides for easier insertion of the proximal sheath 20 into the body vessel by way of the lower friction barrier that is created by the distal sheath 26.

When the hemostatic valve 34 is slid into abutting relationship with the hub 28, as this position is shown in FIG. 6, the proximal sheath 20 is disposed adjacent the distal dilator tip 24 to effectuate a release of the distal sheath 26 from the dilator 22. Put another way, the proximal sheath 20 is advanced to a position such that the releasable attachment between the distal sheath 26 and the dilator 22 is broken. The hub 28 includes a release mechanism 36 configured to release the hub 28 from the support body 12 and effectuate securement of the hub 28 with the hemostatic valve 34. Once the hub 28 and hemostatic valve 34 are secured together, the entire distal sheath 26 overlays the proximal sheath 20 to establish one combined sheath disposed within the body vessel.

Figure 4:
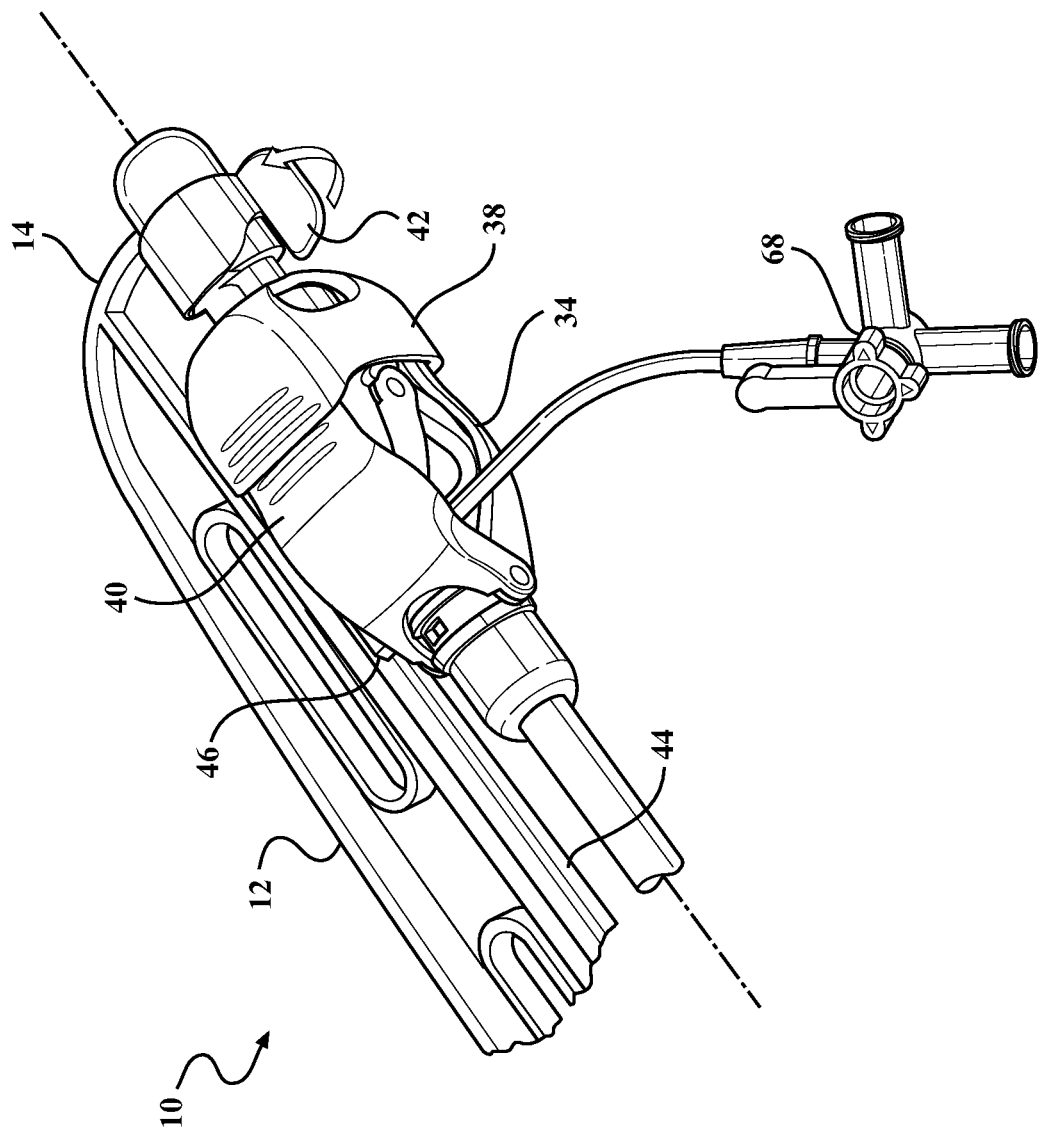
FIG. 4 is a perspective view of a portion of FIG. 3 illustrating the hemostatic valve disposed adjacent a proximal end of a support body and interlocked with a locking member to establish a locked position of the expandable sheath assembly.

In a preferred embodiment, the expandable sheath assembly 10 includes a detachable cap 38 which is snapped or disposed over the hemostatic valve 34 to hold a pair of lever arms 40 in the radially compressed position. This arrangement keeps the hemostatic valve 34 in the open position and facilitates the axial sliding movement of the guide rod 18 through the hemostatic valve 34. As best shown in FIG. 4, in a preferred embodiment, the expandable sheath assembly 10 includes a locking member 42 fixed to the proximal end 14 of the support body 12 and which is configured to establish a locked position of the expandable sheath assembly 10 that prevents axial sliding movement of the hemostatic valve 34 along the guide rod 18. Each of the detachable cap 38 and the locking member 42 can be threaded and the locking member 42 is rotatable about the axis A to threadingly interlock the hemostatic valve 34 to the locking member 42 and establish the locked position of said expandable sheath assembly 10. When a user desires to unlock the expandable sheath assembly 10, the locking member 42 can be rotated about the axis A to unthread the hemostatic valve 34 from the locking member 42 and allow the hemostatic valve 34 to be axially advanced along the guide rod 18 by a user. As further shown in FIG. 4, in a preferred embodiment, the support body 12 can also define a guide track 44 and the detachable cap 38 can define a pair of rails 46 slidably disposed around the guide track 44 for guiding a sliding movement of the hemostatic valve 34 relative to the support body 12.

As mentioned above, when the hemostatic valve 34 is slid into abutting relationship with the hub 28, as this position is shown in FIG. 6, a release mechanism 36 is configured to release the hub 28 from the support body 12 and also effectuate a securement of the hub 28 with the hemostatic valve 34. Although not expressly shown, in a preferred embodiment, a nose cap 48 of the hemostatic valve 34 defines at least one projection and the release mechanism 36 of the hub 28 can define at least notch. When the hemostatic valve 34 is disposed in abutting relationship with the hub 28, the at least one projection is slid into the notch, and the release mechanism 36 is rotated about the axis A to interlock the at least one projection within the hub and establish the secured relationship between the abutting hub 28 and hemostatic valve 34.

As best shown in FIG. 7, the detachable cap 38 can be removed from the hemostatic valve 34 to release the pair of lever arms 40 from the radially compressed position. Once the pair of lever arms 40 are released, a user can manually pull on the support body 12 to slide the guide rod 18 and the dilator 22 along the axis A and out of the proximal sheath 20. This movement separates the support body 12, the guide rod 18, and the dilator 22 from the abutting and secured hemostatic valve 34 and hub 28 which are interconnected to the overlaid distal and proximal sheaths 20, 26. Once the guide rod 18 and dilator 22 are removed from the proximal sheath 20, the proximal sheath 20 which is overlaid with the distal sheath 26 remains within the body vessel and is interconnected to the hemostatic valve 34 disposed outside the body of the patient. As a result, a medical device can now be serially inserted through the hemostatic valve 34 and the proximal sheath 20 and into the body vessel by a user.

In a first arrangement of the expandable sheath assembly, the proximal or introducer sheath 20 is a fixed proximal or introducer sheath having a constant diameter extending along its length. In a preferred arrangement, the constant diameter ranges between 16 FR to 34 FR. However, other constant diameter ranges can also be utilized without departing from the scope of the subject disclosure. The fixed proximal or introducer sheath 20 can be designed and fabricated using known methods such as coextruded tubing or reinforced construction having a PTFE or other low friction polymer liner, reinforced layer and thermoplastic polymer outer jacket. In this embodiment, the fixed proximal or introducer sheath 20 is complementarily sized to the medical device that will be passing through it and into the body vessel. However, in an alternative arrangement of the expandable sheath assembly 10, the proximal or introducer sheath 20 can also be an expandable proximal or introducer sheath. The expandable proximal or introducer sheath is designed to expand as a larger medical device is passed through the expandable proximal sheath and contract when the larger medical device is advanced or removed from the expandable proximal sheath. Put another way, if an expandable proximal sheath is utilized within the expandable sheath assembly 10, the expandable proximal sheath can additionally expand and contract to accommodate a larger size of the medical device when serially inserted through the hemostatic valve 34 and the proximal sheath 20 and into the body vessel.

Referring to the Figures, wherein like numerals indicate corresponding parts throughout the several views, the subject disclosure also includes a method of inserting an expandable sheath assembly 10 into a body vessel of a patient. As best shown in FIGS. 2 and 3, the method begins by inserting a dilator 22 that is overlaid with a distal sheath 26 comprised of a low friction polymeric material into a body vessel of a patient. In a preferred embodiment, and as shown in FIG. 2, a guide wire 66 can be utilized to guide the dilator into the body vessel. Once the dilator 22 is placed within the body vessel, as best shown in FIG. 4, the method proceeds by releasing a hemostatic valve 34 from a proximal end 14 of a support body 12. In a preferred embodiment, the hemostatic valve 34 can be a variable diameter seal hemostatic valve as disclosed in co-owned U.S. patent application Ser. No. 14/326,593 entitled "A Medical Valve with a Variable Diameter Seal", the entire disclosure of which is incorporated by reference. However, other valves, such as iris valves, laproscopic ports, or the like, can also be utilized without departing from the scope of the subject disclosure. The hemostatic valve 34 further includes a proximal sheath 20 extending therefrom and disposed in surrounding and coaxial relationship with a guide rod 18 along an axis A. As shown in at least FIG. 1, a flush port 68 can be in fluid communication with the hemostatic valve 34 for flushing the expandable sheath assembly 10 prior to releasing the hemostatic valve 34 from the proximal end 14 of the support body 12.

Figure 5:
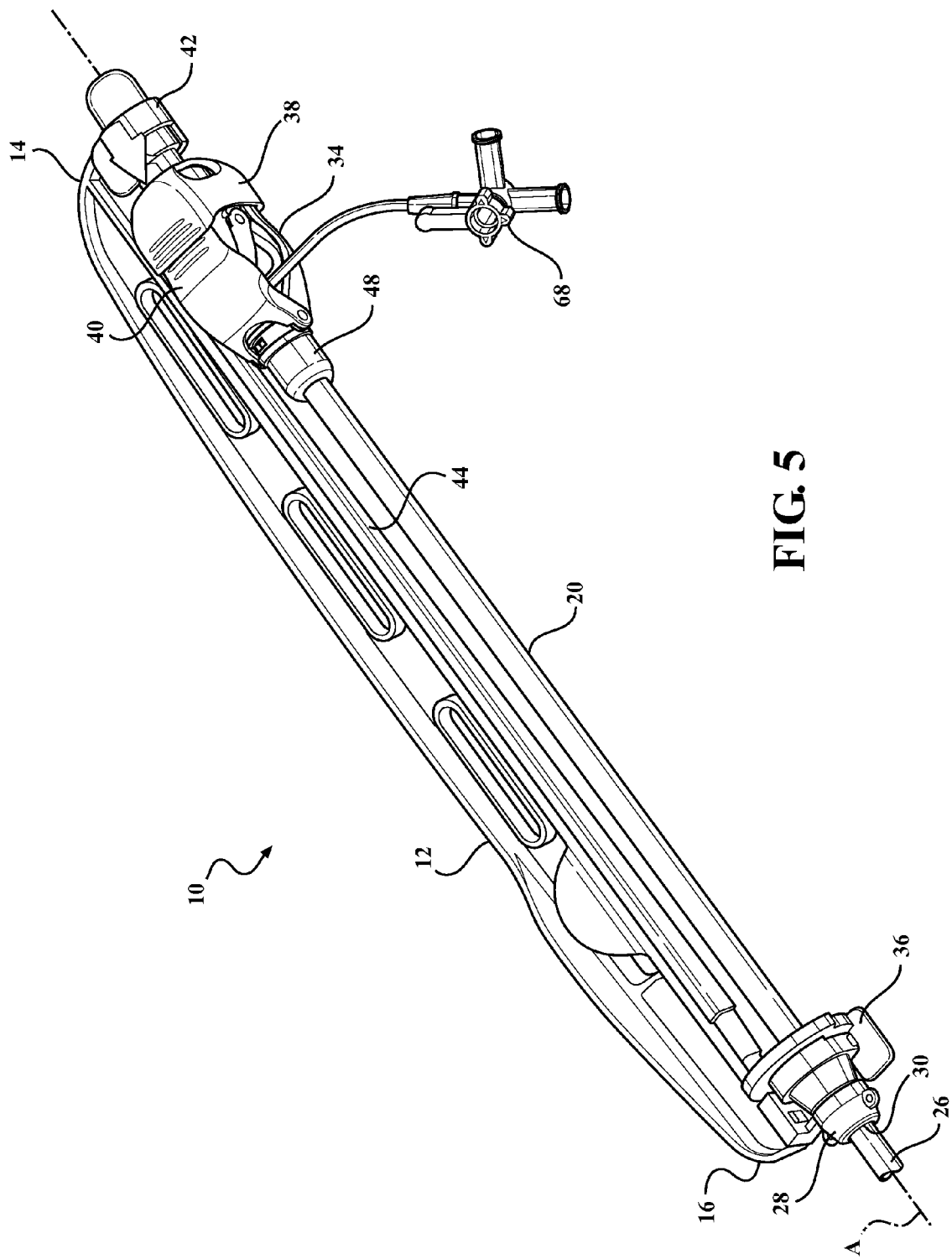
FIG. 5 is a perspective view of the expandable sheath assembly illustrating the hemostatic valve released from the locking member and slidably disposed along an axis A.

As best shown in FIG. 5, once the hemostatic valve 34 is released from the support body 12, the method proceeds by sliding the hemostatic valve 34 along the guide rod 18 to advance the proximal sheath 20 that is attached therewith through a hub 28 disposed about a distal end 16 of the support body 12. In a preferred arrangement, a first distal sheath end 30 of the distal sheath 26 is threadingly attached to the hub 28, and thus the sliding movement of the hemostatic valve 34 through the hub 28 interleaves the proximal sheath 20 between the dilator 22 and the distal sheath 26. This results in a lifting of the distal sheath 26 from the dilator 22 to effectuate an expansion of the body vessel by way of the expanding distal sheath 26. This advantageously allows the proximal sheath 20, which has a larger diameter than a lower profile diameter of the dilator 22, to be slidably advanced into the body vessel. The lifting of the distal sheath 26 to expand the sheath assembly 10 avoids the need to push the proximal sheath 20 past any calcification that is present within the body vessel, and also provides tactile feedback to a user while inserting the proximal sheath 20 into the body vessel.

As best shown in FIG. 6, the method of inserting an expandable sheath assembly 10 into a body vessel proceeds by sliding the hemostatic valve 34 along the guide rod 18 to dispose the hemostatic valve 34 and the hub 38 in abutting relationship with one another. In this abutting position, the proximal sheath 20 is axially advanced past a second distal sheath end 32 of the distal sheath 26 which is releasably attached to the dilator 22. As a result, the proximal sheath 20 breaks the distal sheath 26 from the dilator 22 to effectuate a release of the distal sheath 26 from the dilator 22. Once released from the dilator 22, the distal sheath 26 is disposed in overlaying and surrounding relationship with the proximal sheath 20. The distal sheath 26 acts as a protective layer for the proximal sheath 20 while also providing an easier insertion of the proximal sheath 20 into the body vessel by way of the lower friction barrier established by the distal sheath 26.

As further shown in FIG. 6, the method of inserting an expandable sheath assembly 10 into the body vessel further includes actuating a release mechanism 26 disposed on the hub 28 to release the hub 28 from the support body 12 and secure the abutting hub 28 and hemostatic valve 34 to one another. In a preferred embodiment, when the hemostatic valve 34 is slid into abutting relationship with the hub 28, at least one projection that is disposed on the hemostatic valve 34 is slid into at least one notch defined in the hub 28. As such, the release mechanism 36 is rotated about the axis A to interlock the at least one projection within the hub 28 and establish the secured relationship between the abutting hub 28 and hemostatic valve 34.

As best shown in FIG. 7, the method of inserting an expandable sheath assembly 10 into the body vessel proceeds by releasing a detachable cap 38 from the hemostatic valve 34 to release a pair of lever arms 40 from a radially compressed position. Once the pair of lever arms 40 are released, the method proceeds by manually pulling on the support body 12 to slide the guide rod 18 and the dilator 22 along the axis A and out of the proximal sheath 20. This separates the support body 12, the guide rod 18, and the dilator 22 from the abutting, secured hemostatic valve 34 and hub 28 which are interconnected to the distal and proximal sheaths 20, 26. Once the guide rod 18 and dilator 22 are removed from the proximal sheath 20, the proximal sheath 20 overlaid with the distal sheath 26 remains within the body vessel and is interconnected to the hemostatic valve 34 and the hub 28 which are disposed outside the body of the patient. As a result, a medical device can now be inserted serially through the hemostatic valve 34 and the proximal sheath 20 and into the body vessel. As described above, if an expandable proximal sheath 50 is utilized with the expandable sheath assembly 10, the expandable proximal sheath 50 can additionally expand and contract to accommodate a larger size of the medical device when serially inserted through the hemostatic valve 34 and the expandable proximal sheath 34 and into the body vessel.

The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the disclosure, and all such modifications are intended to be included within the scope of the disclosure.

What is claimed is:

1. A method of inserting an expandable sheath assembly into a body vessel of a patient comprising:
   inserting a dilator overlaid with a distal sheath comprised of a low friction polymeric material into a body vessel of a patient;
   releasing a hemostatic valve from a proximal end of a support body, the hemostatic valve including a proximal sheath extending therefrom and disposed in surrounding and coaxial relationship with a guide rod interconnected to the support body and extending along an axis A; and
   sliding the hemostatic valve along the guide rod from the proximal end of the support body towards a distal end of the support body to advance the proximal sheath through a hub attached to the distal end of the support body effectuating an expansion of the body vessel to allow the proximal sheath to be advanced into the body vessel.

2. A method of inserting an expandable sheath assembly into a body vessel as set forth in claim 1 further comprising:
   sliding the hemostatic valve along the guide rod to dispose the hemostatic valve and the hub in abutting relationship with one another and to axially advance the proximal sheath past a second distal sheath end for effectuating a release of the distal sheath from the dilator and disposing the distal sheath in overlaying and surrounding relationship with the proximal sheath within the body vessel.

3. A method of inserting an expandable sheath assembly into a body vessel as set forth in claim 2 further comprising:
   actuating a release mechanism disposed on the hub to release the hub from the support body and secure the abutting hub and hemostatic valve to one another.

4. A method of inserting an expandable sheath assembly into a body vessel as set forth in claim 3 further comprising:
   said sliding the hemostatic valve into abutting relationship with the hub further includes sliding at least one projection disposed on the hemostatic valve into at least one notch defined in the hub; and
   said actuating the release mechanism includes rotating the release mechanism about the axis A to interlock the at least one projection within the hub.

5. A method of inserting an expandable sheath assembly into a body vessel as set forth in claim 3 further comprising:

releasing a detachable cap from the hemostatic valve to release a pair of lever arms from a radially compressed position; and pulling the support body along the axis A to slide the guide rod and the dilator through the proximal sheath for separating the main body, the guide rod, and the dilator from the abutting hemostatic valve and hub interconnected to the distal and proximal sheaths.

6. A method of inserting an expandable sheath assembly into a body vessel as set forth in claim 5 further comprising:

inserting a medical device serially through the hemostatic valve and the proximal sheath and into the body vessel.

7. An expandable sheath assembly for use in inserting a medical device into a body vessel of a patient comprising:

a support body extending from a proximal end to a distal end;

a guide rod interconnected to said support body and extending between said proximal and distal ends along an axis A;

a dilator extending from said guide rod for initial insertion into a body vessel of a patient;

a hub releasable connected to said distal end of said support body and disposed in surrounding and coaxial relationship with said guide rod;

a distal sheath comprised of a low friction polymeric material overlaying said dilator;

a hemostatic valve slidably disposed about said guide rod and slideable between said proximal and distal ends of said support body; and a proximal sheath extending from said hemostatic valve and disposed in surrounding and coaxial relationship with said guide rod, said proximal sheath concurrently slidable with said hemostatic valve along axis A to advance said proximal sheath through said hub and into said distal sheath for effectuating an expansion of the body vessel.

8. An expandable sheath assembly as set forth in claim 7, wherein said dilator extends from said hub to a distal dilator tip, and said distal sheath extends between a first distal sheath end threadingly attached to said hub and a second distal sheath end releasably secured to said dilator and disposed in spaced relationship with said distal dilator tip.

9. An expandable sheath assembly as set forth in claim 8, wherein said hemostatic valve is slidable along said guide rod to dispose said hemostatic valve and said hub in abutting relationship with one another for axially advancing said proximal sheath past said second distal end to effectuate a release of said distal sheath from said dilator and dispose said distal sheath in overlaying and surrounding relationship with said proximal sheath.

10. An expandable sheath assembly as set forth in claim 9, further comprising a release mechanism disposed on said hub and configured to release said hub from said support body and secure said hub with said abutting hemostatic valve.

11. An expandable sheath assembly as set forth in claim 10, wherein a nose cap of said hemostatic valve defines at least one projection and said release mechanism defines at least one notch for receiving said at least one projection in said abutting relationship of said hub and said hemostatic valve.

12. An expandable sheath assembly as set forth in claim 11, wherein said release mechanism is rotatable to establish said secured relationship of said hub and said abutting hemostatic valve.

13. An expandable sheath assembly as set forth in claim 7, further comprising a detachable cap disposed over said hemostatic valve to hold said hemostatic valve in an open position and facilitate axial sliding movement of said hemostatic valve along said guide rod between said proximal end and said hub.

14. An expandable sheath assembly as set forth in claim 13, wherein said support body defines a guide rail and said detachable cap defines a pair of rails disposed around said guide track for guiding said hemostatic valve along said support body during axial sliding movement along said axis A.

15. An expandable sheath assembly as set forth in claim 13, further comprising:

a locking member fixed to said proximal end of said support body and configured to establish a locked position of said expandable sheath assembly when said hemostatic valve is disposed adjacent said proximal end of said support body.

16. An expandable sheath assembly as set forth in claim 15, where each of said detachable cap and said locking member are threaded and said locking member is rotatable about said axis A to threadingly interlock said hemostatic valve to said locking member and establish said locked position of said expandable sheath assembly.

17. An expandable sheath assembly as set forth in claim 7, wherein said proximal sheath has a fixed diameter in a range of 16 FR to 35 FR.

18. An expandable sheath assembly as set forth in claim 7, wherein said proximal sheath is expandable from a contracted position to an expanded position.

19. An expandable sheath assembly as set forth in claim 7, wherein said low friction polymeric material of said distal sheath comprises expanded polytetrafluoroethylene (ePTFE).

* * * * *